United States Patent [19]

Giuliani et al.

[11] Patent Number: 5,305,492
[45] Date of Patent: Apr. 26, 1994

[54] BRUSH ELEMENT FOR AN ACOUSTIC TOOTHBRUSH

[75] Inventors: David Giuliani, Mercer Island, Wash.; L. David Engel, La Jolla, Calif.

[73] Assignee: Optiva Corporation, Bellevue, Wash.

[21] Appl. No.: 970,761

[22] Filed: Nov. 3, 1992

[51] Int. Cl.⁵ .................... A46B 9/04; A46B 13/02
[52] U.S. Cl. .................... 15/176.1; 15/22.1; 15/167.1; 15/176.6; 15/DIG. 5
[58] Field of Search .............. 15/22.1, 22.2, 167.1, 15/167.2, 176.1, 176.2, 176.3, 176.4, 176.5, DIG. 5, 176.6; 433/216

[56] References Cited

U.S. PATENT DOCUMENTS

| | | | |
|---|---|---|---|
| 1,943,225 | 1/1934 | McIntyre | 15/167.1 |
| 2,917,758 | 12/1959 | Held et al. | 15/22.1 |
| 4,811,445 | 3/1989 | Lagieski et al. | 15/176.6 |
| 4,991,249 | 2/1991 | Suroff | 15/22.1 |
| 5,138,733 | 8/1992 | Bock | 15/167.1 |

FOREIGN PATENT DOCUMENTS

| | | | |
|---|---|---|---|
| 435553 | 10/1967 | Switzerland | 15/22.1 |
| 91/19437 | 12/1991 | World Int. Prop. O. | 15/167.1 |

*Primary Examiner*—Edward L. Roberts
*Attorney, Agent, or Firm*—Jensen & Puntigam

[57] ABSTRACT

The brush element (10) includes a base (14), the base (14) including a connecting portion (18) at one end (16) thereof, which is capable of receiving the lever arm (15) of a vibrating toothbrush. Successive lateral rows of spaced bristles (19–27) are anchored in the brush base (14), in a pattern comprising two successive rows of full length bristles which are configured so that the tips of each two rows form a peak, followed by a third row of shorter bristle portions which are approximately 0.2 inch shorter than the full length bristles.

10 Claims, 1 Drawing Sheet

BRUSH ELEMENT FOR AN ACOUSTIC TOOTHBRUSH

TECHNICAL FIELD

This invention relates generally to the art of power toothbrushes and more specifically concerns a particular brushhead configuration for power toothbrushes.

BACKGROUND OF THE INVENTION

In the art of power toothbrushes, particularly acoustic toothbrushes, an important consideration is the cleaning performance (or lack thereof) of the toothbrush in the interproximal spaces of the teeth, i.e. the spaces between two adjacent teeth and/or the spaces between the teeth and the adjoining gum tissue, down into the subgingival areas beneath the gum line. Acoustic-type power toothbrushes generally have had at least some success in cleaning these interproximal spaces, even though they are beyond the physical reach of the brush elements. Cleaning these interproximal spaces is important, since they harbor pathogenic bacteria and in the case of the gums hence prone to the incidence of periodontal disease.

The success of acoustic toothbrushes in effectively cleaning these regions generally depends upon their ability to disrupt the bacteria in the regions by the agitation of a fluid medium which reaches into the regions, producing sufficient instantaneous velocities and pressures therein so as to damage/disrupt the bacteria. The fluid medium, which could be various combinations of dentifrice, water and saliva, is energized so that instantaneous changes in pressure are produced, giving rise to acoustic effects of cavitation and streaming, which are typically evidenced by the formation of small bubbles visible at the ends of the bristles. This can occur at relatively low sonic frequencies, i.e. in the range of 150Hz-1KHz and at amplitudes which are practical in the mouth. An acoustic toothbrush having the required frequency and instantaneous velocity to produce cavitation and streaming effects is disclosed in co-pending application Ser. No. 832,422, titled "High Performance Acoustical Cleaning Apparatus for Teeth," owned by the same assignee as the present invention.

Proper operation of such a toothbrush requires a relatively high efficiency in order to maintain the cavitation effect. Excessive damping of the bristles must be minimized during the actual brushing operation, so that energy can be efficiently transferred to the fluid. In addition, the brushhead must be configured to effectively and efficiently carry fluid as the toothbrush is moved around the mouth by the user, to ensure that there is sufficient fluid in the area of the brushhead to support agitation. This is frequently an important consideration for the upper teeth especially, where there frequently is a reduced saliva environment.

Various aspects of acoustic toothbrushes have been explored by others to improve damping and fluid movement. This invention is particularly directed toward the brushhead configuration, especially as it affects damping, cavitation, streaming and fluid movement.

DISCLOSURE OF THE INVENTION

Accordingly, the present invention is a brushhead for use with a vibrating toothbrush which uses fluid to produce an acoustic cleaning effect on the teeth beyond the reach of the bristles, wherein the vibrating toothbrush has an operating frequency, the brushhead comprising: a brushhead base member, and a plurality of bristle portions, at least some of the bristle portions being shorter than the remaining longer bristle portions, wherein the remaining bristle portions have a natural resonant frequency such that the operating frequency of the toothbrush is within the range of 0.60 to 0.95 of said natural resonant frequency of the remaining bristle portions.

BEST MODE FOR CARRYING OUT THE INVENTION

Figure 1:
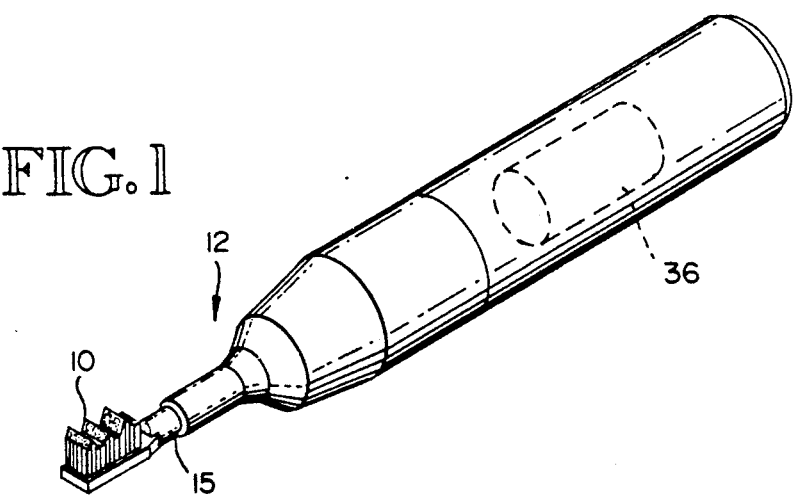
FIG. 1 is a perspective view of the brushhead of the present invention as part of an acoustic toothbrush.

FIG. 1 shows the brushhead of the present invention shown generally at 10 in operative connection to a power toothbrush 12, i.e. at one end of a vibrating lever arm 15. The toothbrush preferably, but not necessarily, operates with a frequency and an acoustical pressure such that bacteria are disrupted and plaque is removed in the proximal (interdental) regions, i.e. the regions between the teeth and/or the subgingival regions between the gum and the teeth. Typically with such a toothbrush, a proper fluid environment is maintained in the mouth so that the acoustic pressure created by the movement of the brushhead is coupled through the fluid to the interdental regions. The bristles will mechanically remove plaque from the exposed areas of the teeth which the bristles actually contact.

The brushhead includes a base portion 14. In the embodiment shown, base portion 14 is approximately 1.5 inches long, 0.3 inches wide, and 0.15 inches thick over the area where the bristles, referred to generally at 17, are anchored. At one end 16 of brushhead 10 is a connecting element 18, which includes a hollow section 20 configured to receive the extending end 13 of lever arm 15. In the embodiment shown, connecting element 18 is somewhat thicker than the remainder of the base portion of the brushhead, in order to provide strength where the brushhead is connected to the lever arm. The brushhead in the embodiment shown also includes nine spaced rows 19-27 of three openings each, to receive the ends of the individual bristles and to facilitate anchoring thereof in brushhead base portion 14.

The particular bristle pattern in the embodiment shown comprises the first two adjacent rows 19, 20 of full length, tapered bristles followed by a third, significantly shorter row 21 of bristles, referred to as background bristles. The fourth and fifth rows 22, 23 are similar to the first and second rows 19 and 20, as are the bristles in the seventh and eighth rows, 25, 26. Likewise, the bristles in the sixth row 24 and in the ninth row 27 are shorter, like row 21, functioning as background bristles.

The full length bristles in rows 19, 20 have a 45° taper at the upper ends thereof, arranged so that the bristles taper downwardly away from an imaginary mid-point between the two rows. A similar arrangement is present in the bristles in rows 4 and 5 as well as rows 7 and 8. Ideally, each bristle strand should be rounded at the upper end thereof, similar to a radius line. In the embodiment shown, the bristles are Tynex, a material like nylon, and are individually stapled or anchored in the openings in the brushhead. In the embodiment shown, there are approximately 25 to 27 individual bristle strands in each opening, defining a tuft of bristles in each opening. The full length bristles in rows 1, 2; 4, 5; and 7, 8 extend approximately 0.45 inches above the surface of the brushhead base portion, while the shorter background bristles in rows 3, 6 and 9 extend approximately 0.25 inches above the surface of the base portion, leaving a difference of approximately 0.2 inches between the full length and the background bristles.

In operation, a drive motor 36 in the body of the power toothbrush will vibrate the lever arm and hence the brushhead at a selected operating frequency. An approximate frequency range is 200–300 Hz. Any of a number of different drive arrangements can be used, including, for instance, the electromagnetic arrangement shown in U.S. Pat. No. 5,189,757 titled "Magnetic Drive Acoustic Toothbrush," which is assigned to the assignee of the present invention. In the embodiment shown, the full length bristles have a natural resonant frequency of approximately 320 Hz. The applicants have discovered that a significant, even critical relationship exists between the operating frequency of the toothbrush (the frequency at which the lever arm is vibrated by the drive motor) and the natural resonant frequency of the full length bristles. It is highly desirable that the operating frequency be in the range of 0.60 to 0.95 of the natural resonant frequency of the full length bristles. More particularly, it is preferred that the operating frequency be approximately 0.80 of the natural resonant frequency.

As an example, for the particular bristles disclosed herein, having a natural resonant frequency of approximately 320 Hz, the operating frequency is approximately 260 Hz, which is approximately 80 percent of the natural resonant frequency of the bristles. An acceptable range is 190 Hz–300 Hz. An operating frequency which is much higher than the upper limit of the specified range (i.e. 300 Hz) will result in a decrease in the actual power delivered to the bristles, apparently due to the higher impedance of the bristles, such that the bristles are in operation too easily damped by the load. If the operating frequency is below the specified range, the bristles will simply be too stiff relative to the vibration frequency and will not have enough flexure to permit efficient movement. This stiffness reduces the ratio of the peak amplitude of the full length bristles (the peak amplitude of the free ends thereof) relative to the bristle base. For best operation, this ratio is within the range of 2.0 to 2.5.

The several rows of shorter bristles have several advantages. First, although the shorter bristles are not long enough to contact the teeth in normal operation, they are long enough and so configured to effectively carry fluid as the brush is moved around in the mouth. Thus, the shorter bristles have an important function relative to maintaining the proper fluid environment for the acoustic toothbrush. In addition, the shorter bristles have a significantly higher resonant frequency than the full length bristles, and thus vibrate with significantly less amplitude, i.e. 0.3 mm, than the full length bristles, which typically have an amplitude of vibration of 3 mm to 5 mm in normal operation. This is because the resonant frequency of the shorter bristles is well outside the preferred frequency range discussed above. The vibrational energy imparted to the brush tends to be concentrated in the full length bristles, since there is little vibrational energy in the movement of the shorter bristles. The rows of shorter bristles being interspersed between the rows of full length bristles has the additional benefit of permitting the full length bristles to more readily spread and then come back together during normal brushing operation, thereby effectively addressing the interproximal spaces of the teeth.

Figure 2:
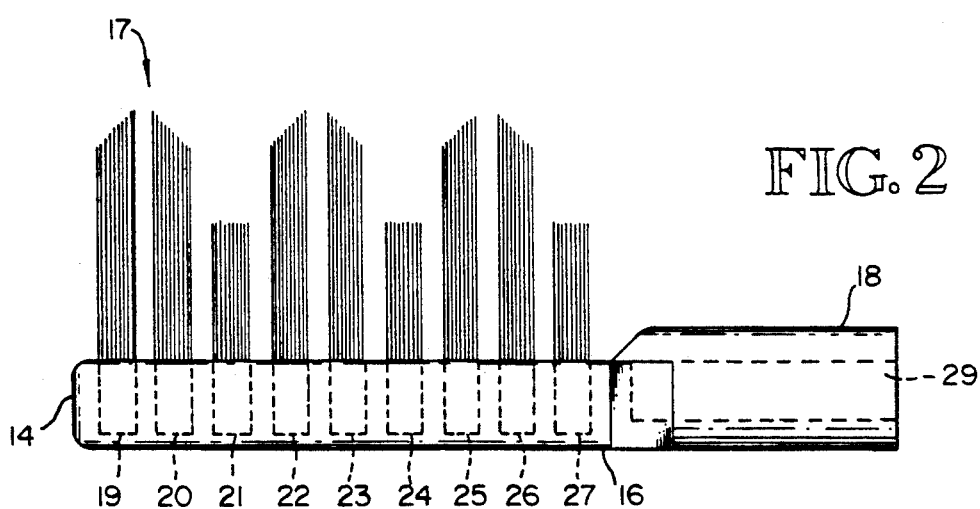
FIG. 2 is a side elevational view of the brushhead of the present invention.
Figure 3:
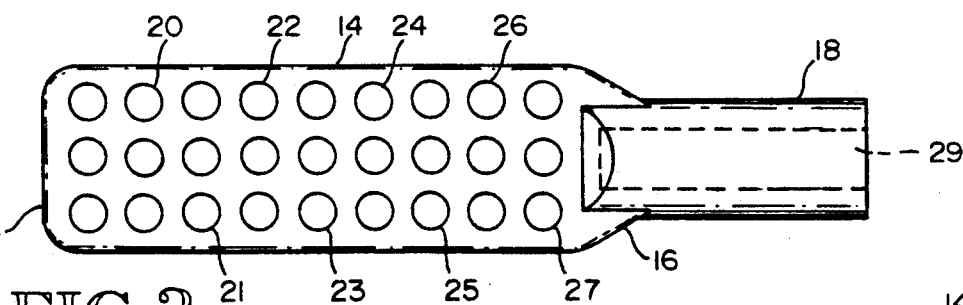
FIG. 3 is a top plan view of the brushhead of FIG. 2.
Figure 4:
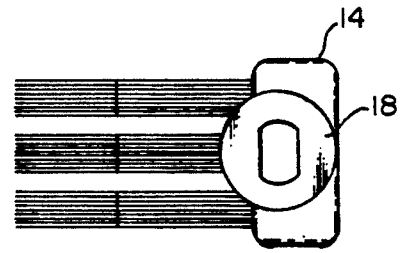
FIG. 4 is an end elevational view of the brushhead of FIGS. 2 and 3.

The particular bristle configuration shown is designed for optimal coverage for molars, incisors and canines. When the peaks of the full length bristles are spaced 0.32 inch apart, they can conveniently reach the interproximal spaces of the second and third molars, which are typically 0.38 to 0.40 inch apart, as well as the upper front teeth. The interproximal spaces of the lower incisors and canines, which are typically 0.20 to 0.30 inch apart, can also be effectively covered. The 45° configuration of the peaks of the bristles (see FIG. 2) permits the bristles to reach into the interproximal gap between the teeth. In operation, the bristles sweep back and forth in this gap, in effect "scraping" plaque from between and on the teeth, as well as providing an acoustical cleaning effect on the bacteria in the interproximal and subgingival regions. The bristles and the two adjacent tooth surfaces defining the interproximal gap create a triangular pocket or zone in which the pressure on the entrapped fluid increases as the bristles sweep back and forth. Performance is increased in this enhanced pressure zone.

In operation, the brush configuration described above is particularly well suited for use with an acoustic toothbrush, since it is configured to be highly efficient and to produce the interproximal contact desired, as well as carrying fluid as the toothbrush moves through the mouth, so that a good fluid environment is maintained to transmit the acoustic pressure created by the vibration of the brush, resulting in the disruption of the bacteria around the teeth.

Although a preferred embodiment of the invention has been disclosed herein for illustration, it should be understood that various changes, modifications and substitutions may be incorporated in such embodiment without departing from the spirit of the invention which is defined by the claims which follow. For instance, the bristle vibration can be back and forth (laterally) or it could be an oscillatory angular movement, or some other vibration pattern.

What is claimed is:

1. A brushhead for use with a vibrating toothbrush which uses fluid to produce an acoustic cleaning effect on the teeth beyond the reach of the bristles, wherein the vibrating toothbrush has an operating frequency in the range of 200 Hz to 300 1 Hz, the brushhead comprising:

a brushhead base member; and a plurality of bristle portions, at least some of the bristle portions being shorter than the remaining, longer bristle portions, wherein the remaining bristle portions have a natural resonant frequency such that the operating frequency of the toothbrush is within the range of 0.60 to 0.95 of said natural resonant frequency of the remaining bristle portions and wherein the shorter bristle portions have a natural resonant frequency significantly greater than the longer bristle portions.

2. An article of claim 1, wherein the shorter bristle portions do not contact the teeth during normal operation of the toothbrush.

3. An article of claim 1, wherein the shorter bristle portions are sufficiently short that they vibrate substantially less in amplitude than the remaining bristle portions.

4. An article of claim 3, wherein the amplitude of vibration of the shorter bristle portions is approximately 0.5 mm and the amplitude of vibration of the longer bristle portions is within the range of 3 mm to 5 mm.

5. An article of claim 1, wherein the operating frequency of the toothbrush is approximately 0.80 percent of the natural resonant frequency of the remaining bristle portions.

6. An article of claim 1, wherein the remaining bristle portions have an angled tip of approximately 45°.

7. An article of claim 1, wherein the bristle portions each comprise a plurality of bristle strands, the bristle portions being arranged in lateral rows, the brushhead including a plurality of rows of bristle portions, with a selected pattern of shorter bristle portions and longer bristle portions.

8. An article of claim 7, wherein the selected pattern comprises a sequence of two rows of longer bristle portions followed by one row of shorter bristle portions.

9. An article of claim 1, wherein the shorter bristle portions are at least 0.2 inch shorter than the longer bristle portions.

10. An article of claim 1, wherein the longer bristle portions have tips, and wherein the tips of successive longer bristle portions are spaced approximately 0.3 inch apart.

* * * * *